United States Patent
Cheng et al.

(10) Patent No.: US 11,896,836 B2
(45) Date of Patent: Feb. 13, 2024

(54) CONVEYING DEVICE, CARDIAC PACING DEVICE, AND FIXING STRUCTURE THEREOF

(71) Applicant: MICROPORT SOARING CRM (SHANGHAI) CO., LTD., Shanghai (CN)

(72) Inventors: Zhijun Cheng, Shanghai (CN); Grace Jang, Shanghai (CN); Li Wang, Shanghai (CN)

(73) Assignee: MICROPORT SOARING CRM (SHANGHAI) CO., LTD., Shanghai (CN)

(*) Notice: Subject to any disclaimer, the term of this patent is extended or adjusted under 35 U.S.C. 154(b) by 71 days.

(21) Appl. No.: 17/271,870

(22) PCT Filed: Aug. 30, 2019

(86) PCT No.: PCT/CN2019/103839
§ 371 (c)(1),
(2) Date: Feb. 26, 2021

(87) PCT Pub. No.: WO2020/043205
PCT Pub. Date: Mar. 5, 2020

(65) Prior Publication Data
US 2021/0260386 A1    Aug. 26, 2021

(30) Foreign Application Priority Data
Aug. 31, 2018  (CN) .......................... 201811011695.8

(51) Int. Cl.
*A61N 1/375* (2006.01)
*A61N 1/05* (2006.01)

(52) U.S. Cl.
CPC ........... *A61N 1/3756* (2013.01); *A61N 1/057* (2013.01); *A61N 1/37512* (2017.08); *A61N 1/37518* (2017.08); *A61N 2001/058* (2013.01)

(58) Field of Classification Search
CPC .. A61N 1/3756; A61N 1/057; A61N 1/37512; A61N 1/37518; A61N 2001/058; A61N 1/362
See application file for complete search history.

(56) References Cited

U.S. PATENT DOCUMENTS 5,179,962 A * 1/1993 Dutcher ............... A61N 1/0573
607/128
5,314,462 A * 5/1994 Heil, Jr. ............... A61N 1/0573
607/128

(Continued)

FOREIGN PATENT DOCUMENTS

CN    103328040 A    9/2013
CN    105536137 A    5/2016

(Continued)

*Primary Examiner* — Eugene T Wu
(74) *Attorney, Agent, or Firm* — Muncy, Geissler, Olds & Lowe, P.C.

(57) ABSTRACT

A delivery device, a cardiac pacing device and a fixation structure are disclosed. The fixation structure includes a casing, a driving member and an elastic member. The casing has a first internal cavity and a slot, and the driving member is partially received in the first internal cavity in such a manner that one end of the driving member protrudes out of the first internal cavity from a proximal end thereof and is detachably connected to the driving sheath. The elastic member is accommodated in the first internal cavity in such a manner that its one end is coupled to the driving member and the other end extends outwardly from the driving member and is inserted in the slot. The driving member is configured for fitted connection with the casing while being able to move in an axial direction of the casing to drive the (Continued)

elastic member to move in the slot, thereby causing the elastic member to protrude out of or move back into the slot. As such, the cardiac pacing device can be fixed in a patient's body, allows retrieval and adjustment in pacing location, and features a simple structure, ease of operation, no limitation in tissue wall thickness and ease of fixation. Thus, the leadless pacing device can be fixed either in a ventricle or in an atrium to provide dual-chamber pacing and physiological pacing with atrioventricular synchronization.

14 Claims, 10 Drawing Sheets

(56) References Cited

U.S. PATENT DOCUMENTS

| | | | |
|---|---|---|---|
| 2009/0082828 A1 | 3/2009 | Ostroff | |
| 2011/0251660 A1 | 10/2011 | Griswold | |
| 2012/0172690 A1* | 7/2012 | Anderson | A61N 1/0573 607/18 |
| 2013/0296957 A1 | 11/2013 | Tronnes | |
| 2018/0104449 A1 | 4/2018 | Arnar et al. | |
| 2018/0133465 A1 | 5/2018 | Orts et al. | |

FOREIGN PATENT DOCUMENTS

| | | |
|---|---|---|
| CN | 106362288 A | 2/2017 |
| CN | 107233665 A | 10/2017 |
| CN | 107583187 A | 1/2018 |
| CN | 108310652 A | 7/2018 |

* cited by examiner

CONVEYING DEVICE, CARDIAC PACING DEVICE, AND FIXING STRUCTURE THEREOF

TECHNICAL FIELD

The present invention relates to the field of medical instruments and, in particular, to a delivery device, a cardiac pacing device and a fixation structure thereof.

BACKGROUND

Since the advent in 1958, cardiac pacemakers have become a first-line treatment for bradycardia arrhythmias. With the advancements and innovations over the past more than half century, cardiac pacemaker have gradually evolved from the initial form of single leads for open chest implantation and ventricular pacing to the recent form of 2-3 leads for intravenous implantation and atrioventricular physiological pacing or even biventricular synchronous pacing. Nevertheless, lead-related complications such as lead dislodgement, thrombosis, tricuspid regurgitation and infection have for long not only interrupted the application of pacemakers, but also seriously threatened patients' health and lives and degraded their quality of life. For patients found with lead-related complications, it is necessary to remove the leads from them as soon as possible. However, as such lead removal operations are associated with certain difficulties and risks, they usually have to be performed in large electrophysiology centers by dexterous surgeons, imposing great burden on resource utilization and surgeons' workload. In order to overcome these problems arising from the use of leads, "leadless" cardiac pacemakers have become a new focus of interest in the field of arrhythmia treatment.

Leadless pacemakers usually include a fixation mechanism that is separate from a pacing electrode and has a diameter equal to or smaller than an outer diameter of the pacemaker. The fixation mechanism allows the pacemaker to be inserted into heart tissue by rotating two revolutions so that the pacing electrode is brought into contact with the tissue and fixed. Some leadless pacemakers further include a circular ring-shaped feature disposed at a proximal end of the leadless pacemaker, which can tether the leadless pacemaker within the right ventricle upon the failure of the distal fixation mechanism of the leadless pacemaker, preventing its entry into the blood circulation system and consequent danger to the patient. Each of these leadless pacemakers is implanted into the heart by delivering it to the right ventricular apex using a delivery system and then rotating it so that a helical feature at a distal end thereof screws into the relative thick apical myocardial tissue. However, fixation of such a leadless pacemaker relying on the screwing action of the helical feature to the atrial wall that is very thin will be associated with severe hazards such as insecure fixation, atrial perforation, etc. Since all these existing leadless pacemakers have to be fixed to the right ventricular apex, they are only suitable for univentricular pacing and incapable of dual-chamber pacing (a DDD pacing mode). Therefore, the existing leadless pacemakers tend to suffer from non-physiological pacing with atrioventricular de synchronization.

SUMMARY OF THE INVENTION

In view of this, it is an objective of the present invention to provide a delivery device, a cardiac pacing device and a fixation structure thereof, which are not limited to any tissue wall thickness, capable of easy fixation and arrhythmia treatment through either atrial or ventricular pacing, i.e., dual-chamber pacing, simple in structure and allows retrieval and adjustment in pacing location.

According to one aspect of the present invention, there is provided a fixation structure, including:
- a casing having a first internal cavity and a slot, the slot extending radially and formed in an external surface of the casing so as to be in communication with the first internal cavity;
- a driving member partially accommodated in the first internal cavity, one end of the driving member protruding out of the first internal cavity from a proximal end thereof; and
- an elastic member accommodated in the first internal cavity, one end of the elastic member coupled to the driving member and the other end extending outwardly from the driving member and being inserted in the slot,
- wherein the driving member is configured for fitted connection with the casing while being able to move in an axial direction of the casing to drive the elastic member to move in the slot, thereby causing the elastic member to protrude out of or move back into the slot.

Additionally, the driving member may define an external thread and an inner wall of the casing that corresponds to the first internal cavity defines an internal thread engageable with the external thread, wherein the elastic member is configured to move circumferentially relative to the driving member.

Additionally, the fixation structure may further include:
- a gasket defining a central hole, through which the gasket is disposed over a distal end of the driving member, thereby limiting an axial displacement of the elastic member.

Additionally, the end of the driving member protruding out of the first internal cavity may have a shape of a polygonal prism.

Additionally, the proximal end of the casing may have a shape of a polygonal prism.

Additionally, the fixation structure may further include:
- a first limiting element configured to limit a distance of movement of the driving member toward a distal end of the casing; and/or
- a second limiting element configured to limit a distance of movement of the driving member toward a proximal end of the casing.

Additionally, the first internal cavity may be a T-shaped cavity including an upper surface and a lower surface opposing the upper surface, wherein the upper surface forms the first limiting element, and the lower surface forms the second limiting element.

Additionally, the driving member may include a limiting portion located at a distal end of the driving member, wherein the limiting portion includes opposing first and second surfaces, wherein the first surface of the limiting portion is configured to abut against the upper surface of the first internal cavity, and wherein the second surface of the limiting portion is configured to abut against the lower surface of the first internal cavity.

Additionally, the limiting portion may be cross-shaped or T-shaped.

Additionally, the fixation structure may include a plurality of the elastic members, which are spaced apart from one another around an axis of the driving member.

Additionally, the elastic member may be elongated and have a sharp tip configured to penetrate into a target object.

Additionally, the slot may be inclined toward a proximal or distal end of the casing.

Additionally, the casing may further have a second internal cavity that is separate from the first internal cavity in the axial direction of the casing.

According to another aspect of the present invention, there is provided a cardiac pacing device including the fixation structure according to any of the preceding paragraphs; and a leadless pacemaker arranged on the fixation structure.

Additionally, the casing of the fixation structure may further have a second internal cavity that is separate from the first internal cavity in the axial direction of the casing, wherein the leadless pacemaker includes:

a control member disposed in the second internal cavity of the casing; and at least two electrodes, each of which is connected to the control member, arranged on the casing and configured to be brought into contact with the target object.

According to a further aspect of the present invention, there is provided a delivery device for delivering the cardiac pacing device as defined above, which includes:

a loading sheath having a distal end configured for detachable connection with the proximal end of the casing; and a driving sheath having a distal end configured for detachable connection with the end of the driving member protruding out of the first internal cavity, wherein the driving sheath is moveably inserted in the loading sheath and configured to cooperate with the loading sheath to deliver the cardiac pacing device to a target site and drive the driving member to move relative to the casing.

Additionally, the distal end of the loading sheath may define a first polygonal bore configured for fitted connection with the proximal end of the casing, which has a shape of a polygonal prism, and the distal end of the driving sheath may define a second polygonal bore configured for fitted connection with the end of the driving member protruding out of the first internal cavity, which has a shape of a polygonal prism.

Compared with the prior art, the delivery device, cardiac pacing device and fixation structure provided in the present invention offer the following benefits:

First, the driving member in the cardiac pacing device is driven to move by the delivery device, thus causing the elastic member to move forward or backward in the slot of the casing. As such, the elastic member is made telescopable—when the end of the elastic member extends out of the slot, it can penetrate into the wall of a tissue at a target site in a patient's body, thus fixing the cardiac pacing device at the target site; and when the end of the elastic member moves back into the slot, retrieval of the cardiac pacing device is allowed, thus allowing the delivery device to adjust the pacing location and fix it at the best pacing location during implantation.

Second, the engagement of the threads respectively in the driving member and the casing can convert their rotational movement to axial movement for driving the elastic member to move forward or backward in the slot. This design is simple in structure and allows ease of operation.

Third, the elastic member is elongated and has a sharp tip, which can directly penetrate into the tissue wall essentially without being limited to any particular tissue wall thickness. Moreover, a depth of the penetration can be adjusted by telescopic movement, making the fixation more convenient. Therefore, the leadless pacing device can be fixed either in a ventricle or in an atrium to provide dual-chamber pacing and physiological pacing with atrioventricular synchronization.

BRIEF DESCRIPTION OF THE DRAWINGS

The accompanying drawings are presented in order to provide a better understanding of the present invention without limiting it in any way. In these figures.

In these figures,

10—cardiac pacing device; 11—casing; 11a—first segment; 11b—second segment; 111—slot; 112—first internal cavity; 113—upper surface; 114—lower surface; 115—second internal cavity; 12—driving member; 121—first end; 122—second end; 121—limiting portion; 13—elastic member; 131—third end; 132—fourth end; 14—first electrode; 15—second electrode; 16—gasket;

20—delivery device; 21—loading sheath; 22—driving sheath;

30—guide device; 31—expansion sheath; 32—guide sheath;

A—inferior vena cava; RA—right atrium; B—superior vena cava.

DETAILED DESCRIPTION OF PREFERRED EMBODIMENTS

The above and other objects, features and advantages of the present invention will become more apparent upon reading the following more detailed description of the proposed delivery device, cardiac pacing device and fixation structure, which is to be read in conjunction with FIGS. 1 to 10. Note that the figures are provided in a very simplified form not necessarily presented to scale, with their only intention to facilitate convenience and clarity in explaining the disclosed embodiments.

The terms "proximal" and "distal" will be used herein to describe relative orientations, relative positions or directions of components or actions with respect to one another, from the perspective of a physician using a medical instrument. While not meant to be limiting, a "proximal end" of the medical instrument generally refers to the end thereof that is located closer to the physician when in a normal operating state of the instrument, while a "distal end" of the instrument generally refers to the end thereof that enters the body of a patient first. The term "internal" or "internally" generally refers to a direction toward an axis of a driving member, while the term "external" or "externally" refers to a direction away from the axis of the driving member.

As used herein and in the appended claims, the singular forms "a", "an", and "the" include plural references unless the context clearly dictates otherwise. As used herein and in the appended claims, the term "or" is generally employed in its sense including "and/or" unless the content clearly dictates otherwise.

Figure 1:
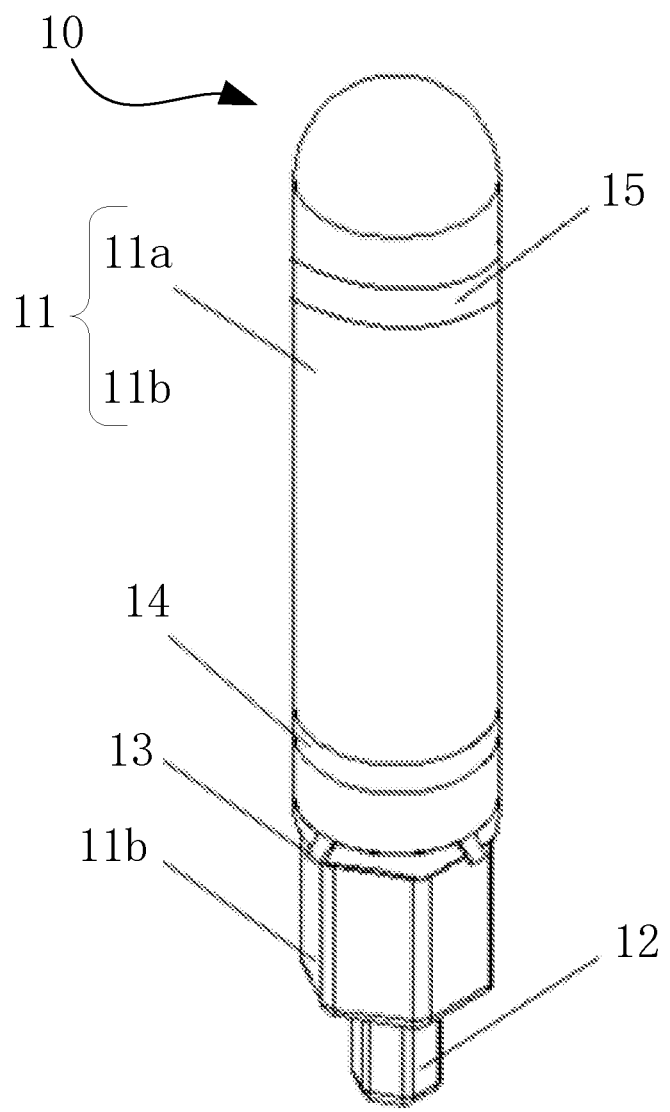
FIG. 1 is a perspective view of a cardiac pacing device according to an embodiment of the present invention.
Figure 2:
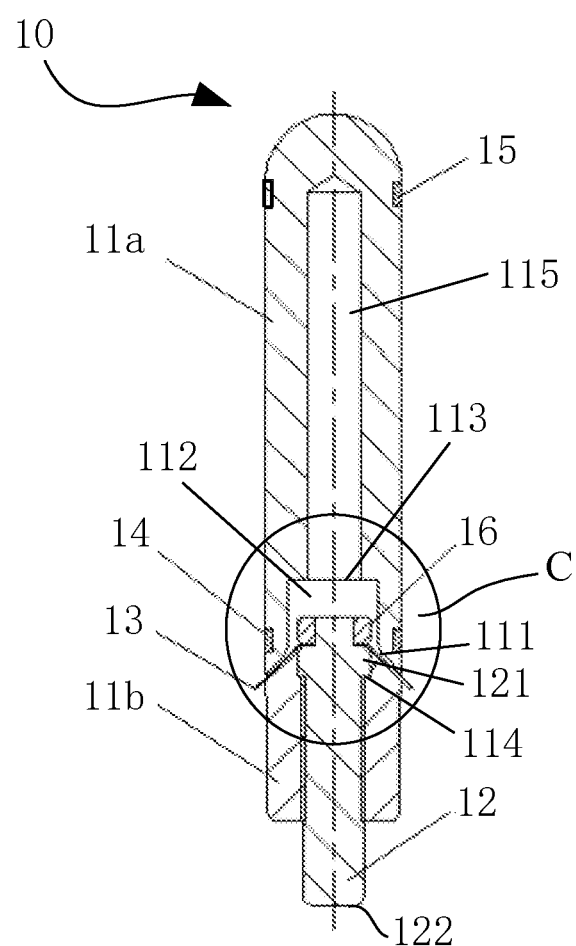
FIG. 2 is an axial cross sectional view of the cardiac pacing device of FIG. 1.
Figure 3:
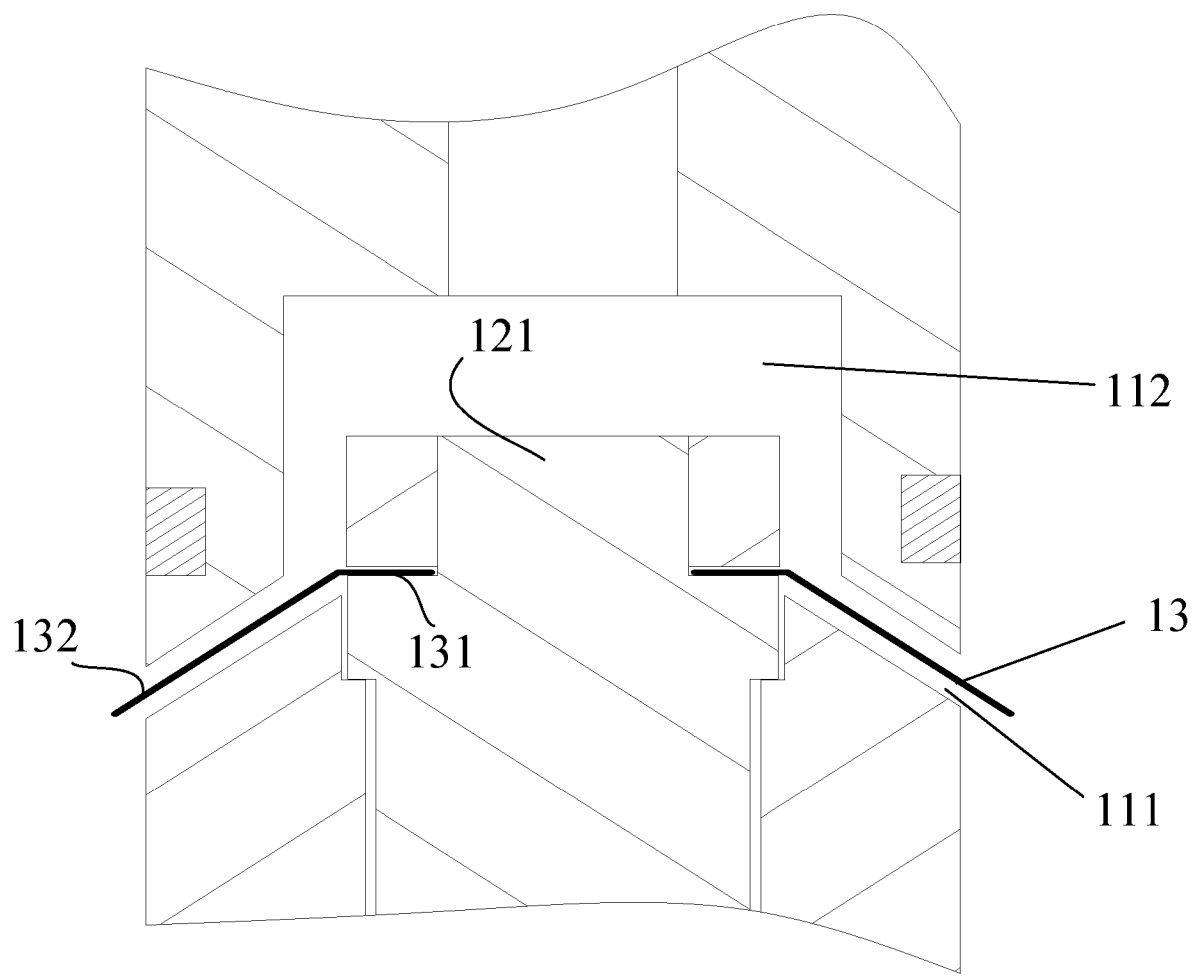
FIG. 3 is an enlarged view of portion C of the cardiac pacing device of FIG. 2.

FIG. 1 is a perspective view of a cardiac pacing device according to an embodiment of the present invention. FIG. 2 is an axial cross sectional view of the cardiac pacing device of FIG. 1. FIG. 3 is an enlarged view of portion C of the cardiac pacing device of FIG. 2. As shown in FIGS. 1 to 3, the cardiac pacing device 10 according to this embodiment is used to relieve arrhythmia through either atrial or ventricular pacing.

Specifically, the cardiac pacing device 10 includes a fixation structure (not shown) and a leadless pacemaker arranged on the fixation structure. The fixation structure includes a casing 11, a driving member 12 and an elastic member 13. The leadless pacemaker includes control member (not shown) and at least two electrodes.

The control member may include, among others, an impulse generator, a communication module, a battery and a processor. The impulse generator may be configured to provide pacing impulses and deliver the pacing impulses to a first electrode 14. The first electrode 14 may transmit the pacing impulses further to the myocardium to cause its contraction. The communication module may communicate with an external device wirelessly and thus establish a wireless connection for data exchange. In some embodiments, the communication module may receive commands from an external programmer and transmit the commands to the processor, which may then modulate the impulse generator to adjust the impulses output by the impulse generator. As a key component of the leadless pacemaker, the processor may be configured to perform various functions including data storage, data output and scheduling between various modules. Upon receiving electrical signals representative of atrial or ventricular activity from a second electrode 15, the processor may perform a computation on the electrical signals and modulate the impulse generator based on the computation results so that desired changes occur in the output impulses. The battery may be configured to power, and ensure normal operation of, the impulse generator, the communication module, the processor and other electronic components necessary for the operation of the cardiac pacemaker.

In one embodiment, the two electrodes are the first and second electrodes and may be connected to the control member. The first electrode may function as a pacing electrode and the second electrode as a sensing electrode. The first and second electrodes may be connected individually to the control member, the first and second electrodes may be connected to each other. During operation of the leadless pacemaker, the control member and the first and second electrodes may together form a loop for cardiac pacing or sensing. In other embodiments, more electrodes may be included to impart additional capabilities to the leadless pacemaker. For the sake of brevity, the following description is given in the context of two electrodes, i.e., the first and second electrodes 14, 15. A person skilled in the art would be able to adapt the following description for cases with more than two electrodes by making appropriate modifications in details.

The casing 11 is configured to house and seal the leadless pacemaker and is preferably in the shape of a capsule. Alternatively, it may also be a cuboid, an ellipsoid, a polygonal prism or the like and is most desirable to be space-saving. In an external surface of the casing 11, a radially-extending slot 111 is formed, and the slot 111 is in communication with a first internal cavity 112 in the casing 11. Here, the term "radially-extending" shall not be interpreted narrowly as being limited to extending of the slot 111 perpendicularly to an axial direction of the casing. Rather, it shall be interpreted broadly as extending of the slot 111 not along the axial direction of the casing 11. In case of the slot 111 extending radially at an angle with respect to the casing, the slot 111 can be inclined toward either a proximal end (see FIG. 2) or a distal end of the casing 11.

The driving member 12 is configured to drive the elastic member 13 to move in the slot 11, and is partially received in the first internal cavity 112 of the casing 11 in such a manner that the first end 121 of the driving member 12 is located within the first internal cavity 112, with its second end 122 protruding out of the first internal cavity 112 from a proximal end thereof and being connected to the driving sheath 22 detailed below. The driving member 12 is further configured for fitted connection with the casing 11 while being able to move at least axially relative to the casing 11. Here, the term "fitted connection" is meant to mean that the two components stay stationary with respect to each other when there is no external force acting thereon or there is an external force not exceeding a predetermined limit Preferably, the driving member 12 is able to rotate about the axial direction relative to the casing 11, and the rotation can be converted to the axial translation.

The elastic member 13 is accommodated within the first internal cavity 112 of the casing 11 in such a manner that a third end 131 of the elastic member 13 is connected to the driving member 12, and a fourth end 132 of the elastic member 13 extends outwardly from the driving member 12 and is inserted in the slot 111. When the driving member 12 moves axially with respect to the casing 11, the portion of the elastic member 13 in the slot 111 will be caused to move, so that the fourth end 132 of the elastic member 13 will protrude out of the slot 111 and penetrate into the wall of a tissue at a target site, thus fixing the cardiac pacing device 10 at the target site in the body. Of course, movement in the opposite direction will remove the fourth end 132 of the elastic member 13 from the tissue wall and retract it back into the slot 111, facilitating retrieval and re-positioning of the cardiac pacing device 10. According to the present invention, the elastic member 13 has good elastic deformability, which allows the elastic member 13 to move forward or backward in the direction of extension of the slot 111 under the action of the driving member 12. The elastic member 13 is preferably elongated and is preferred to be a thin sheet. More preferably, the fourth end 132 of the elastic member 13 includes a sharp tip capable of penetrating into the tissue wall (i.e., a target object). The elastic member 13 is made preferably of a super-elastic shape memory.

According to the present invention, the second end 122 of the driving member 12 may be configured for detachable connection with the driving sheath 22, and the proximal end of the casing 11 may be also configured for detachable connection with a loading sheath 21. In this way, the cardiac pacing device 10 can be delivered into the patient's body by the delivery device 20 detailed below.

In order to bring each of the first and second electrodes 14, 15 into contact with the heart muscle, it may be fastened to the casing 11 in such a manner that it is partially received within the casing, with the remainder being located out of the casing 11 and brought into contact with the myocardium, or in such a manner that it is entirely situated outside the casing and is assured to be brought into contact with the myocardium. The control member may be configured for pacing and sensing control of the cardiac pacemaker. The second electrode 15 may be configured to transmit electrical signals representative of atrial or ventricular activity to the control member, and the first electrode 14 may be configured to receive pacing impulse signals for atrial or ventricular pacing from the control member.

Figure 4:
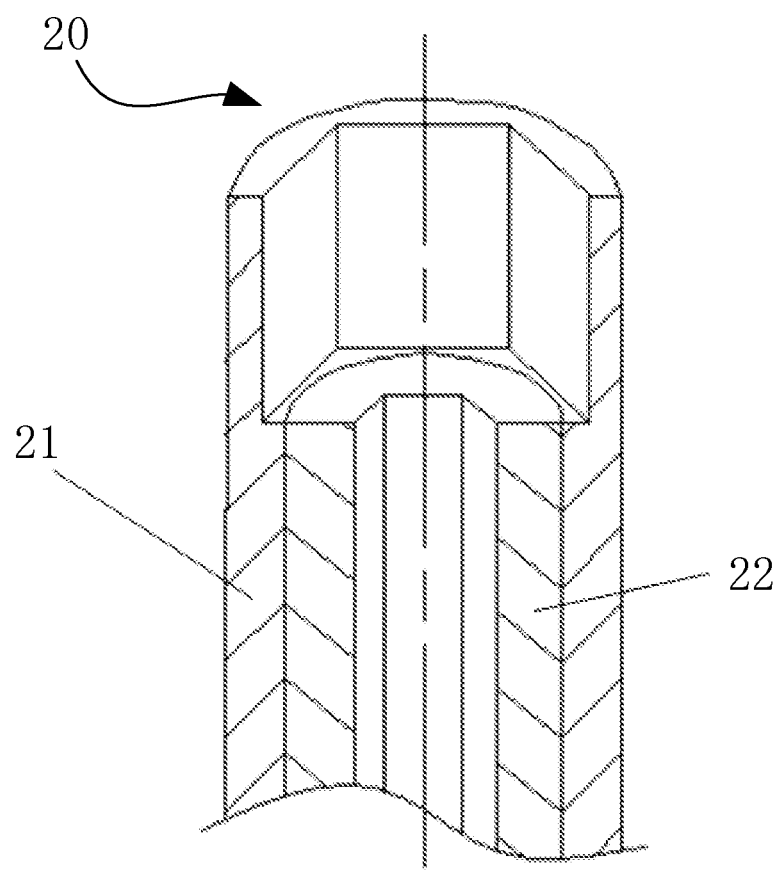
FIG. 4 is a partial axial cross-sectional view of a delivery device according to an embodiment of the present invention.

FIG. 4 is a partial axial cross-sectional view of a delivery device according to an embodiment of the present invention. As shown in FIG. 4, the present invention further provides with a delivery device 20, the delivery device 20 includes a loading sheath 21 and a driving sheath 22. The driving sheath 22 is configured to be inserted in the loading sheath 21 such as to be able to move axially relative to the loading sheath 21. In practical use, a distal end of the loading sheath 21 is detachably connected to the proximal end of the casing 11, and a distal end of the driving sheath 22 is detachably connected to the second end 122 of the driving member 12.

Figure 5:
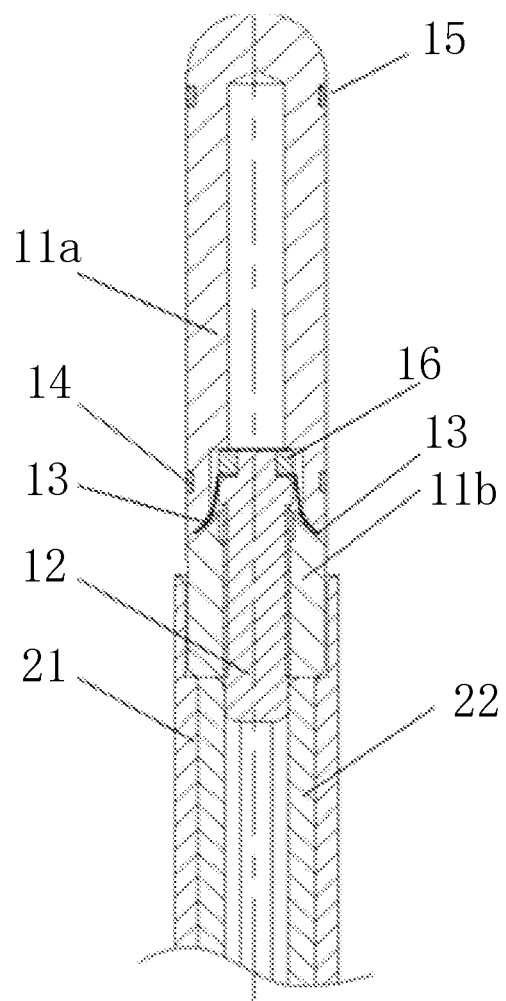
FIG. 5 is an axial cross-sectional view illustrating how the delivery device is connected to the cardiac pacing device according to an embodiment of the present invention.

FIG. 5 is an axial cross-sectional view illustrating how the delivery device is connected to the cardiac pacing device according to an embodiment of the present invention. As shown in FIG. 5, prior to implantation, the cardiac pacing device 10 may be assembled with the delivery device 20 (in practice, the cardiac pacing device 10 may be arranged at the distal end of the delivery device 20), and the loading sheath 21 (and hence the casing 11 connected to the loading sheath 21) may be held still. The driving sheath 22 may be then driven to move axially (e.g., by rotating it about the axial direction) relative to the loading sheath 21, thereby causing the driving member 12 to move axially relative to the casing 11 (from the view of FIG. 5, this corresponds to upward movement of the driving member 12 toward the distal end of the casing 11) until the elastic member 13 is entirely received in the casing 11.

Figure 6:
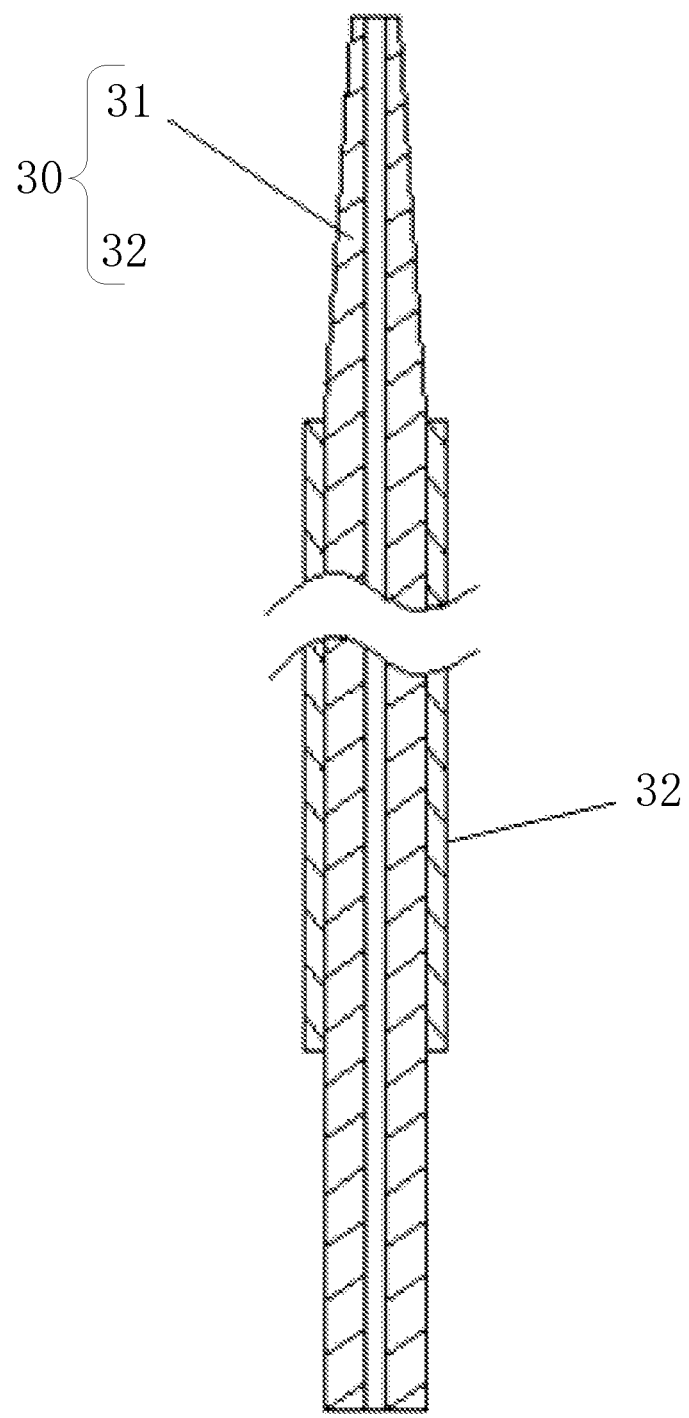
FIG. 6 is an axial cross-sectional view of a guide device according to an embodiment of the present invention.

FIG. 6 is an axial cross-sectional view of a guide device according to an embodiment of the present invention. As shown in FIG. 6, the present invention further provides with a guide device 30 which is configured to create a delivery channel in the patient's body in advance for delivery of the delivery device 20 therein up to the target site in the patient's body.

The guide device 30 may include an expansion sheath 31 and a guide sheath 32. The expansion sheath 31 may be inserted in the guide sheath 32 so as to be moveable in the guide sheath 32. The expansion sheath 31 may define an axial lumen in which a guide wire can be inserted.

Figure 7:
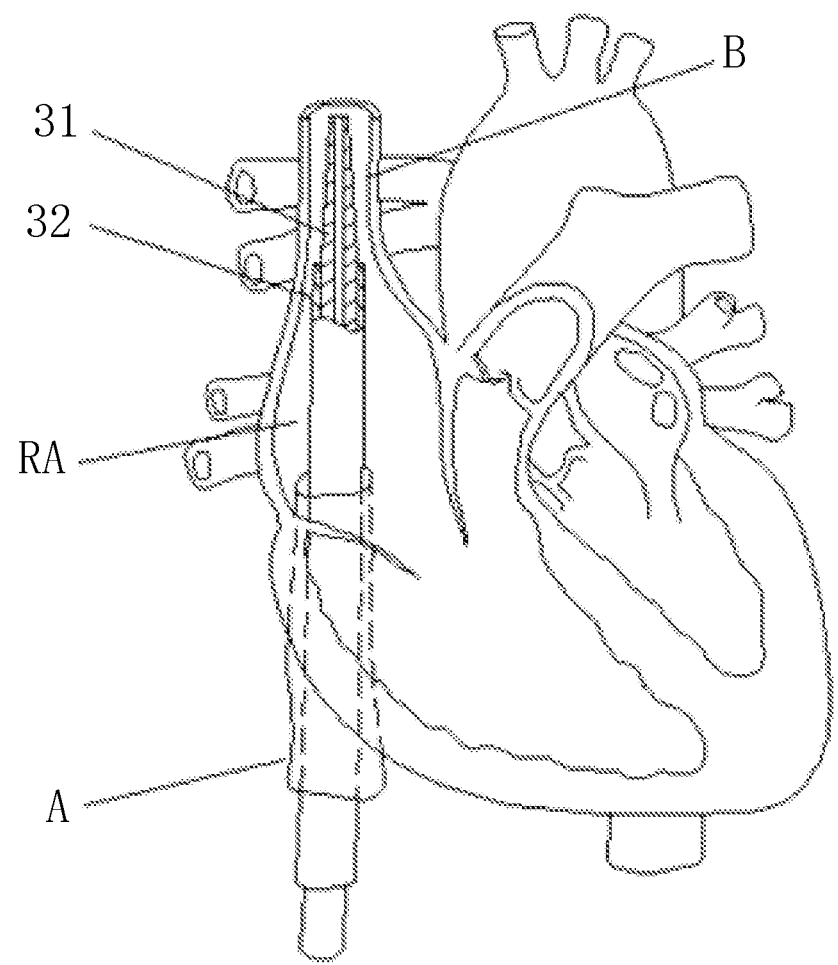
FIG. 7 schematically illustrates how an expansion sheath and a guide sheath are introduced via the femoral vein across the inferior vena cava and the right atrium up to the superior vena cava according to an embodiment of the present invention.
Figure 8:
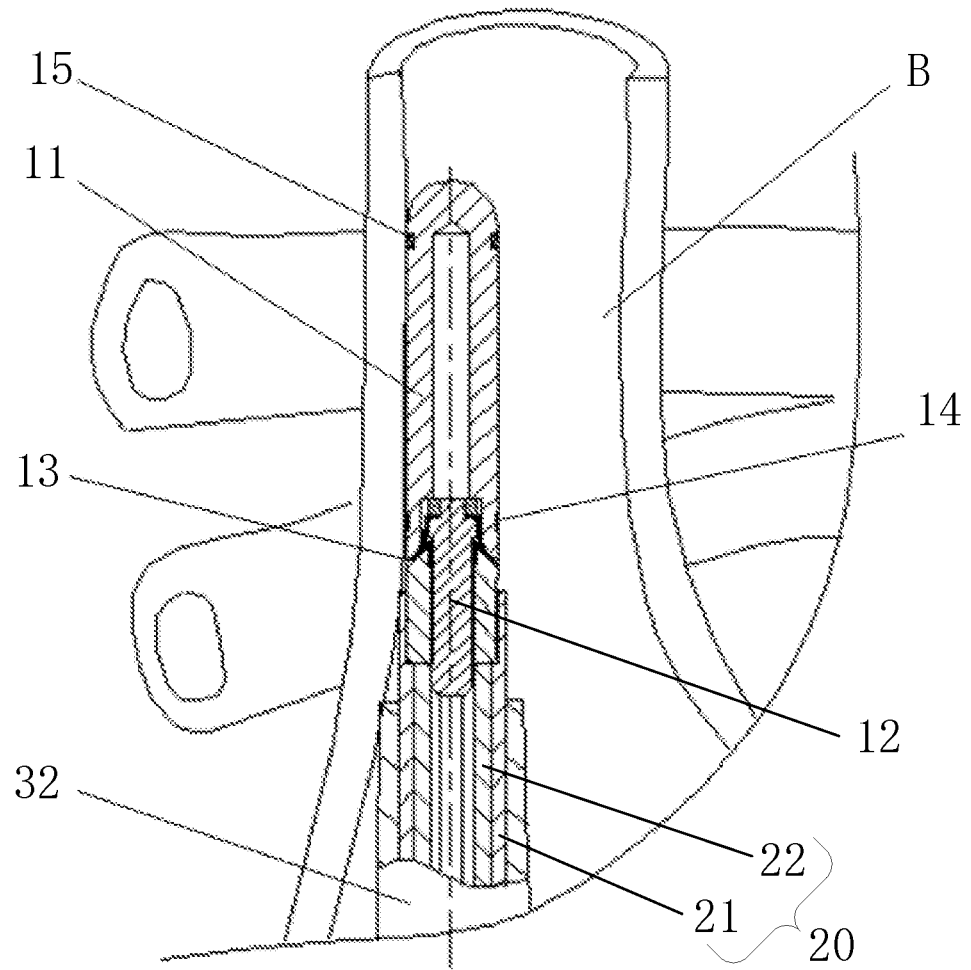
FIG. 8 schematically illustrates the cardiac pacing device that has been delivered into the superior vena cava using the guide sheath according to an embodiment of the present invention.
Figure 9:
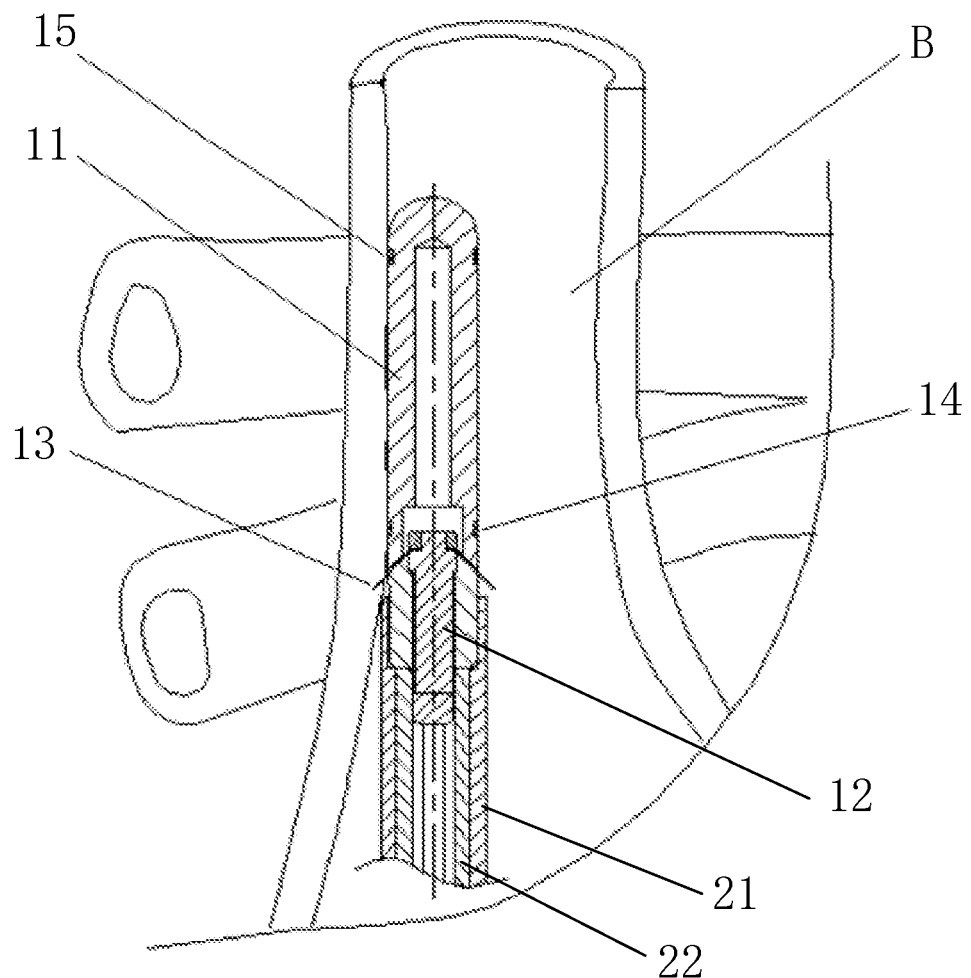
FIG. 9 schematically illustrates an elastic member which has extended out of a slot and penetrated into the superior vena cava wall according to an embodiment of the present invention.
Figure 10:
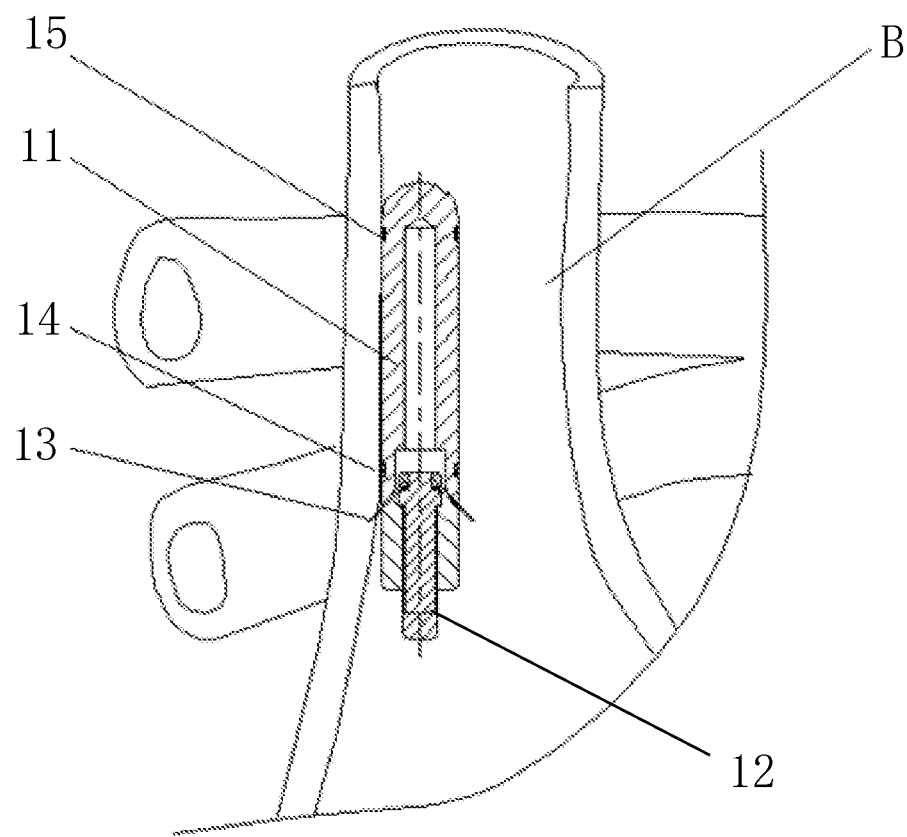
FIG. 10 schematically illustrates the cardiac pacing device that is alone fixed in the superior vena cava according to an embodiment of the present invention.

Specifically, as shown in FIG. 7, the expansion and guide sheaths 31, 32 may be introduced via the femoral vein across the inferior vena cava A and the right atrium RA up to the superior vena cava B. The expansion sheath 31 may be then withdrawn, with the guide sheath 32 being retained. Afterwards, as shown in FIG. 8, the delivery device 20 connected to the cardiac pacing device 10 may be loaded into the guide sheath 32 from the proximal end of the guide sheath 32 and then advanced until the distal end of the delivery device 20 reaches the superior vena cava B (i.e., arrival of the cardiac pacing device 10 at the superior vena cava B). In addition, as shown in FIG. 9, with the loading sheath 21 being held still, the driving sheath 22 may be driven to move (differing from FIG. 5, from the view of FIG. 9, this corresponds to downward movement of the driving member 12 toward the proximal end of the casing 11), causing the fourth end 132 of the elastic member 13 to penetrate into the wall of the superior vena cava and bringing the second and first electrodes 15, 14 into contact with the inner wall of the superior vena cava B. Subsequently, a test may be performed to access pacing and sensing electrical parameters under the control of an external program. If the test results of the pacing and sensing electrical parameters are unfavorable, the cardiac pacing device 10 may be relocated accordingly. During the relocation of the cardiac pacing device 10, the loading sheath 21 may be held still, concurrently with the driving sheath 22 being driven to move in the opposite direction (from the view of FIG. 9, this corresponds to upward movement of the driving member 12). As a result, the fourth end 132 of the elastic member 13 will be pulled off the blood vessel wall and move back into the slot 111, thereby allowing the cardiac pacing device 10 to be relocated in the superior vena cava B by the delivery device 20. The relocation of the cardiac pacing device 10 may be accomplished, for example, by causing synchronized axial or circumferential movement of the loading and driving sheaths 21, 22. Upon the results of test on pacing and sensing electrical parameters being found satisfactory after one or more runs of such adjustment, the fourth end 132 of the elastic member 13 may be caused to protrude out and penetrate into the blood vessel wall in the same manner as described above. In this way, adjustment in pacing location can be accomplished. At last, as shown in FIG. 10, all the guide sheath 32, loading sheath 21 and driving sheath 22 may be withdrawn from the patient's body, making the completion of the implantation of the cardiac pacing device. In the same way, dual-chamber pacing allowing physiological pacing with atrioventricular synchronization can be achieved by fixing the cardiac pacing device 10 to, but not limited to, the junction between the superior vena cava and the right atrium, the inferior vena cava, or the junction between the inferior vena cava and the right atrium.

As can be seen from the above description, according to the present invention, the elastic member 13 can be caused to move forward or backward in the slot 111 of the casing 11 under the driving action of the driving member 12 in the cardiac pacing device 10, which is in turn driven by the delivery device 20. In this way, the elastic member 13 is made telescopable so that when the fourth end 132 of the elastic member 13 extends out of the slot 111 and penetrates into the tissue wall, the cardiac pacing device 10 can be fixed at the target site in the patient's body, and when the fourth end 132 of the elastic member 13 moves back into the slot 111, the cardiac pacing device 10 can be retrieved, thus allowing the delivery device 20 to adjust the pacing location and fix the cardiac pacing device 10 at the best pacing location during the implantation of the cardiac pacing device 10.

In addition, the first and second electrodes 14, 15 may be disposed at the respective opposing ends of the casing 11. This allows a simple structure and thus easy fabrication of the casing. For example, the first electrode 14 may be arranged at the proximal end of the casing 11 and the second electrode 15 at the distal end of the casing 11. However, the present invention is not limited to any particular arrangement of the two electrodes, and the two electrodes can also be otherwise arranged as actually required by the treatment, for example, at a single end of the casing 11, as long as they can be brought into contact with the tissue wall and function as expected. In embodiments of the present invention, the second and first electrodes 15, 14 may be arranged on the first segment 11a detailed below and respectively at distal and proximal ends of the first segment 11a.

Further, any one of the first and second electrodes 14, 15 is preferably provided circumferentially around the external surface of the casing 11, so that it can have an increased contact surface with the tissue wall and enhanced performance.

The fixation structure may further include at least one of a first limiting element and a second limiting element. The first limiting element may be configured to define a limit for movement of the driving member 12 toward the distal end of the casing 11, while the second limiting element may be configured to define a limit for movement of the driving member 12 toward the proximal end of the casing 11. In this way, the lengths the elastic member 13 can extend out from the slot and retract back into the slot can be strictly controlled. It should be understood that, in the case of the slot 111 being inclined toward the proximal end of the casing, the second limiting element may be configured to limit the length the elastic member 13 can extend out from the slot 111, while the first limiting element may be configured to limit the length the elastic member 13 can move back into the slot 111. In the case of the slot 111 being inclined toward the distal end of the casing, the second limiting element may be configured to limit the length the elastic member 13 can move back into the slot 111, while the first limiting element may be configured to limit the length the elastic member 13 can extend out from the slot 111. As such, movement of the driving member 12 can be limited in the range between the first and second limiting elements.

Preferably, the first internal cavity 112 in the casing 11 is a blind bore. In this case, the first limiting element may be provided by a distal end of the first internal cavity 112. Preferably, the first internal cavity 112 may be shaped like the letter T and consist of two parts having different cross-sectional areas. Moreover, the driving member 12 may be moveably disposed within the part with the larger cross-sectional area, and this part may have an upper surface 113 forming the first limiting element, and a lower surface 114 opposing the upper surface 113 and forming the second limiting element. Further, axial movement of the driving member 12 may be limited to the range between the top and lower surfaces 113, 114.

Correspondingly, the driving member 12 may include a limiting portion 121 (preferably disposed at the first end of the driving member) having a horizontal surface configured to abut against the lower surface 114 and another horizontal surface configured to abut against the upper surface 113. Preferably, without limitation, the limiting portion 121 may be cross-shaped. Alternatively, the limiting portion 121 may also be T-shaped.

The casing 11 may further define an axially-extending second internal cavity 115 in communication with the first internal cavity 112 or not. In this case, the control member may be disposed within the second internal cavity 115. In the case of the second internal cavity 115 being in communication with the first internal cavity 112, in order to form the first limiting element, a cross-sectional area of the second internal cavity 115 may be smaller than those of the first internal cavity 112, and a cross-sectional area of the limiting portion 121 at the other horizontal surface configured to abut against the upper surface 113 may be greater than the cross-sectional area of the second internal cavity 115. The first and second internal cavities 112, 115 are preferred to be arranged coaxially, and the second internal cavity 115 preferably has a closed distal end.

Further, the casing 11 may include a first segment 11a and a second segment 11b both arranged along the axial direction. Preferably, the first and second segments 11a, 11b are separately fabricated and then coupled together by welding, bonding or the like. More preferably, the slot 111 is formed where the first and second segments 11a, 11b are connected to each other, for example, by laser cutting or putting them together. Alternatively, after the first segment 11a and the second segment 11b are connected, the slot 111 is formed directly, i.e., notches may be formed respectively at a proximal end of the first segment 11a and a distal end of the second segment 11b and may delimit the slot 111 when the two notches are put together. The second internal cavity 115 may be defined in the first segment 11a, while the first internal cavity 112 may be defined partly in the first segment 11a and partly in the second segment 11b.

Further, the fitted connection between the driving member 12 and the casing 11 is preferably accomplished by threads. Relative rotation of the threads can be converted to axial movement, which may cause the elastic member 13 to move forward or backward. Specifically, the driving member 12 may define an external thread engageable with an internal thread formed in an inner wall of the casing 11, which corresponds to the first internal cavity 112. When the driving sheath 22 is rotated about the axial direction by an external force, the driving member 12 will be caused to rotate about the axial direction relative to the casing 11 by means of fitted connection of the driving sheath 22 with the second end 122 of the driving member 12, and this rotational movement will be converted to relative axial movement by the aforementioned threads. It will be recognized that, during the rotational movement about the axial direction, both the loading sheath 21 and the casing 11 are kept stationary. In addition, the elastic member 13 may be configured to move circumferentially relative to the driving member 12 with the rotation of the driving member 12 about the axial direction. That is, the elastic member 13 may move circumferentially in synchronization with the driving member 12 or not. For example, when the driving member 12 rotates about the axial direction, the elastic member 13 may be kept stationary circumferentially with respect to the driving member 12.

The fixation structure 110 may further include a gasket 16 fixed at the first end 121 of the driving member 12. The gasket 16 may be configured to cooperate with the driving member 12 to limit axial displacement of the elastic member 13 relative to the driving member 12. Specifically, the elastic member 13 may be partially received in a slit delimited by the gasket 16 and the limiting portion 121 and configured to be axially stationary and circumferentially movable relative to the driving member 12, in order to ensure that the elastic member 13 can move forward or backward freely in the slot 111. The gasket 16 may be an annulus, and the first end 121 of the driving member 12 may be inserted through a central hole of the gasket 16 and thus fixed to the gasket 16.

Preferably, a plurality, for example, two, three or more, of the elastic members 13 may be provided and spaced apart from one another around the axis of the driving member 12. In the case of the driving member 12 being able to rotate about the axial direction, the elastic members 13 may be configured to be circumferentially moveable relative to the driving member 12. The elastic members 13 may be integrally arranged on an annular body in such a manner that they are distributed around an axis of the body. Preferably, the body may define a hole, through which the body may be disposed over the driving member and between the gasket 16 and the limiting portion 121 such as to be circumferentially rotatable. In alternative embodiments, the elastic members 13 may be inverted L-shaped and pressed between the gasket 16 and the limiting portion 121.

A plurality of the slots 111 may be provided, and the number of them may be either equal to that of the elastic members 13 or not. For example, each elastic member 13 may be moveable forward or backward within a respective one of the slots 111. Alternatively, multiple adjacent elastic members 13 may be moveable forward or backward within a single slot 111. It should be understood that the slots 111 may be spaced apart from one another on the casing 11 in order to ensure continuity of the casing 11.

In embodiments of the present invention, the fitted connection of the second end 122 of the driving member 12 with the driving sheath 22 is preferably form-fitted connection. For example, the second end 122 of the driving member 12 may be configured as a polygonal prism, and the driving sheath 22 may define a corresponding polygonal bore, which opens distally and is engageable with the polygonal prism. In this case, the external thread may be formed in the driving member 12 at a portion other than the first and second ends 121, 122.

Correspondingly, the second segment 11*b* of the casing 11 may also be configured as a polygonal prism adapted for fitted connection with a polygonal blind bore formed at the distal end of the loading sheath 21. In this way, fixed connection of the casing 11 to the loading sheath 21 can be achieved. The loading sheath 21 may further define a through hole formed in the polygonal blind bore, in which the driving sheath 22 can be inserted.

However, according to the present invention, the fitted connection between the driving member 12 and the casing 11 is not limited to being accomplished by a threaded fit, because it can also be accomplished otherwise, for example, by a spring latch or a snap fastener, as long as the driving member 12 can be driven to move axially relative to the casing 11 that is being kept stationary. In addition, both the connection between the casing 11 and the loading sheath 21 and that between the driving member 12 and the driving sheath 22 are not limited to being accomplished by a polygonal prism and a mating polygonal bore, and other means for making detachable connection are also possible, such as, for example, threads, spring latches, snap fasteners, etc., as long as they can couple the pairs of components together and allow their decoupling as necessary. Further, the components including the expansion sheath 31, the guide sheath 32, the loading sheath 21 and the driving sheath 22 are all preferably made of a polymer material. Additionally, the structure for limiting the range of movement for the driving member 12 is not limited to the T-shaped first internal cavity, and other structures may also be possible, such as a protrusion or a slot. Furthermore, the slot 111 may have an arcuate shape. In this case, at least portion of the elastic member 13 received in the slot 111 has a corresponding arcuate shape.

In summary, according to embodiments of the present invention, the driving member is preferably driven by spiral movement to rotate about the axial direction relative to the casing. This design is simple in structure and allows ease of operation. In addition, according to the present invention, the elastic member is essentially an elongated thin sheet with a sharp tip, which can fix the cardiac pacing device at a target site by effectively penetrating into the wall of a tissue at the target site without being limited to any particular tissue wall thickness. Moreover, telescopic movement of the elastic member allows adjustment in a penetration depth of the elastic member for any particular fixation requirement, making the fixation more flexibly. Thus, the leadless pacing device can be fixed either in a ventricle or in an atrium to provide dual-chamber pacing and physiological pacing with atrioventricular synchronization.

It is apparent that those skilled in the art can make various modifications and variations to the present invention without departing from the spirit and scope thereof. Accordingly, the invention is intended to embrace all such modifications and variations if they fall within the scope of the appended claims and equivalents thereof.

What is claimed is:

1. A fixation structure, comprising:
a casing having a first internal cavity and a slot, the slot extending radially and formed in an external surface of the casing so as to be in communication with the first internal cavity;
a driving member partially accommodated in the first internal cavity, one end of the driving member protruding out of the first internal cavity from a proximal end thereof; and
an elastic member accommodated in the first internal cavity, one end of the elastic member coupled to the driving member and the other end extending outwardly from the driving member and being inserted in the slot,
wherein the driving member is configured for fitted connection with the casing while being able to move in an axial direction of the casing to drive the elastic member to move in the slot, thereby causing the elastic member to protrude out of or move back into the slot, and
wherein the driving member defines an external thread and an inner wall of the casing that corresponds to the first internal cavity defines an internal thread engageable with the external thread, wherein the elastic member is configured to move circumferentially relative to the driving member.

2. The fixation structure according to claim 1, further comprising a gasket defining a central hole, through which the gasket is disposed over a distal end of the driving member, thereby limiting an axial displacement of the elastic member.

3. The fixation structure according to claim 1, wherein the end of the driving member protruding out of the first internal cavity has a shape of a polygonal prism.

4. The fixation structure according to claim 1, wherein the proximal end of the casing has a shape of a polygonal prism.

5. The fixation structure according to claim 1, further comprising:
a first limiting element configured to limit a distance of movement of the driving member toward a distal end of the casing; and/or
a second limiting element configured to limit a distance of movement of the driving member toward a proximal end of the casing.

6. The fixation structure according to claim 5, wherein the first internal cavity is a T-shaped cavity comprising an upper surface and a lower surface opposing the upper surface, the upper surface forming the first limiting element, the lower surface forming the second limiting element.

7. The fixation structure according to claim 6, wherein the driving member comprises a limiting portion located at a distal end of the driving member, the limiting portion comprising opposing first and second surfaces, the first surface of the limiting portion configured to abut against the upper surface of the first internal cavity, the second surface of the limiting portion configured to abut against the lower surface of the first internal cavity.

8. The fixation structure according to claim 7, wherein the limiting portion is cross-shaped or T-shaped.

9. The fixation structure according to claim 1, wherein the fixation structure comprises a plurality of the elastic members, which are spaced apart from one another around an axis of the driving member.

10. The fixation structure according to claim 1, wherein the elastic member is elongated and has a sharp tip configured to penetrate into a target object.

11. The fixation structure according to claim 1, wherein the slot is inclined toward a proximal or distal end of the casing.

12. The fixation structure according to claim 1, wherein the casing further has a second internal cavity that is separate from the first internal cavity in the axial direction of the casing.

13. A cardiac pacing device, comprising:
the fixation structure according to claim 1; and
a leadless pacemaker arranged on the fixation structure.

14. The cardiac pacing device according to claim 13, wherein the casing of the fixation structure further has a second internal cavity that is separate from the first internal cavity in the axial direction of the casing, and
wherein the leadless pacemaker comprises:
a control member disposed in the second internal cavity of the casing; and
at least two electrodes, each of which is connected to the control member, arranged on the casing and configured to be brought into contact with the target object.

* * * * *